(12) United States Patent
Stadelmann et al.

(10) Patent No.: US 11,291,827 B2
(45) Date of Patent: Apr. 5, 2022

(54) ELECTROPORATION DEVICE HAVING A BATTERY PACK WITH POWER SWITCH

(71) Applicant: Inovio Pharmaceuticals, Inc., Plymouth Meeting, PA (US)

(72) Inventors: Beat Stadelmann, San Diego, CA (US); Stephen Kemmerrer, San Diego, CA (US)

(73) Assignee: Inovio Pharmaceuticals. Inc., Plymouth Meeting, PA (US)

( * ) Notice: Subject to any disclaimer, the term of this patent is extended or adjusted under 35 U.S.C. 154(b) by 880 days.

(21) Appl. No.: 16/065,315

(22) PCT Filed: Dec. 22, 2016

(86) PCT No.: PCT/US2016/068413
§ 371 (c)(1),
(2) Date: Jun. 22, 2018

(87) PCT Pub. No.: WO2017/112898
PCT Pub. Date: Jun. 29, 2017

(65) Prior Publication Data
US 2021/0162201 A1    Jun. 3, 2021

Related U.S. Application Data

(60) Provisional application No. 62/270,998, filed on Dec. 22, 2015.

(51) Int. Cl.
*A61N 1/04* (2006.01)
*A61N 1/30* (2006.01)
(Continued)

(52) U.S. Cl.
CPC .......... *A61N 1/0412* (2013.01); *A61N 1/303* (2013.01); *A61N 1/327* (2013.01); *H01M 50/204* (2021.01); *H01M 50/247* (2021.01)

(58) Field of Classification Search
None
See application file for complete search history.

(56) References Cited

U.S. PATENT DOCUMENTS

| 5,569,550 | A | 10/1996 | Garrett et al. |
| 2007/0087637 | A1 | 4/2007 | Zart et al. |
| (Continued) | | | |

FOREIGN PATENT DOCUMENTS

| CN | 1905920 A | 1/2007 |
| CN | 101939047 A | 1/2011 |
| (Continued) | | |

*Primary Examiner* — Brian T Gedeon
(74) *Attorney, Agent, or Firm* — BakerHostetler

(57) ABSTRACT

An electroporation device having a battery pack including a plurality of battery cells and at least one lead in electrical communication with a circuit board. The battery pack including a safety switch and a controller for selectively placing the battery cells in electrical communication with the one lead. Where the controller is in operable communication with the safety switch such that when the controller detects one or more operating conditions the controller instructs the safety switch to electrically isolate the lead from the battery cells. The battery pack also includes a manual switch, and where activation of the switch causes the controller to instruct the safety switch to electrically isolate the lead from the battery cells.

18 Claims, 4 Drawing Sheets

(51) Int. Cl.
*A61N 1/32* (2006.01)
*H01M 50/204* (2021.01)
*H01M 50/247* (2021.01)

(56) References Cited

U.S. PATENT DOCUMENTS

| | | |
|---|---|---|
| 2008/0106238 A1 | 5/2008 | Ragsdale |
| 2009/0015208 A1 | 1/2009 | White et al. |
| 2009/0030364 A1 | 1/2009 | Harmon et al. |
| 2009/0184682 A1 | 7/2009 | Kosugi et al. |
| 2010/0147700 A1 | 6/2010 | Field et al. |
| 2010/0152761 A1 | 6/2010 | Mark |
| 2011/0009807 A1 | 1/2011 | Kjeken et al. |
| 2011/0040235 A1* | 2/2011 | Castel .................. A61M 37/00 604/20 |
| 2011/0121110 A1 | 5/2011 | Field |
| 2012/0070338 A1 | 3/2012 | Schaeffer et al. |
| 2014/0222105 A1 | 8/2014 | Broderick et al. |
| 2015/0094914 A1 | 4/2015 | Abreu |
| 2015/0265825 A1* | 9/2015 | Miller .................... A61N 1/325 604/20 |

FOREIGN PATENT DOCUMENTS

| | | |
|---|---|---|
| CN | 102256629 A | 11/2011 |
| CN | 103492018 A | 1/2014 |
| CN | 103687644 A | 3/2014 |
| CN | 103861202 A | 6/2014 |
| JP | 10-513601 A | 12/1998 |
| JP | 2007-213987 A | 8/2007 |
| JP | 2008-062064 A | 3/2008 |
| JP | 2012-512007 A | 5/2012 |
| JP | 2014-524796 A | 9/2014 |
| RU | 2141853 C1 | 11/1999 |
| WO | 2013/066427 A1 | 5/2013 |
| WO | 2014/115183 A1 | 7/2014 |
| WO | WO-2015/089492 | 6/2015 |
| WO | 2015/127466 A2 | 8/2015 |

* cited by examiner

ELECTROPORATION DEVICE HAVING A BATTERY PACK WITH POWER SWITCH

CROSS-REFERENCE TO RELATED APPLICATIONS

This patent application is the National Stage Application of International Patent Application No. PCT/US2016/068413, filed Dec. 22, 2016, which claims priority to U.S. Provisional Patent Application No. 62/270,998, filed Dec. 22, 2015. The above referenced applications are hereby incorporated by reference in their entirety.

BACKGROUND

Embodiments of the invention relate to an electroporation device with a battery pack; and more specifically an electroporation device with a battery pack with a power switch formed therein.

SUMMARY OF THE INVENTION

Handheld medical devices, such as handheld electroporation devices, include battery packs to provide operational power. In some handheld medical devices, the battery packs are directly soldered to circuit boards within the handheld medical devices to reduce electrical losses and save space. During the manufacturing process, the battery packs are capable of instantaneously supplying electrical power upon being soldered to the circuit boards. The ability to instantaneously supply electrical power can cause undesirable operating conditions (for example, short circuits) when the battery packs are installed on the circuit boards.

Conventionally, electrical components (i.e., resistors or switches) are coupled to the circuit board to prevent the battery packs from causing undesirable operating conditions upon being installed on the circuit boards. However, such electrical components tend to be larger in physical size and can cause undesirable effects on the performance of the battery packs and the handheld medical devices.

In one aspect, a handset of an electroporation device, the handset including a housing defining a volume therein, a circuit board at least partially positioned within the volume, an electrode extending from the housing and in electrical communication with the circuit board, and a battery pack. The battery pack including a battery pack housing, a plurality of battery cells positioned within the battery pack housing, a first power lead in electrical communication with the circuit board, a second power lead coupled to the plurality of battery cells and in electrical communication with the circuit board, a safety switch positioned within the battery pack housing and coupled between the first power lead and the plurality of battery cells, where the safety switch is adjustable between an ON state, where the plurality of battery cells are in electrical communication with the first power lead, and an OFF state, where the plurality of battery cells are not in electrical communication with the first power lead.

In another aspect, a handset of an electroporation device, the handset including a housing, an injection assembly, a circuit board at least partially positioned within the housing and in operable communication with the injection assembly, an electrode extending from the housing and in electrical communication with the circuit board, and a battery pack. The battery pack including a battery housing at least partially positioned within the housing, a plurality of battery cells positioned within the battery pack housing, a first power lead in electrical communication with the circuit board, a second power lead coupled to and extending between the plurality of battery cells and the circuit board, a safety switch operable coupled between the first power lead and the plurality of battery cells, where the safety switch is adjustable between an ON state, where the plurality of battery cells are in electrical communication with the first power lead, and an OFF state where the plurality of battery cells are not in electrical communication with the first power lead, and a controller in operable communication with the safety switch, the controller configured to detect one or more operating conditions, and where the controller is configured to adjust the safety switch between the ON state and the OFF state based at least in part on the detected operating conditions.

In still another aspect, an electroporation device including a base station, and a handset removably coupled to the base station. The handset including a housing, an injection assembly, a circuit board at least partially positioned within the housing and in operable communication with the injection assembly, an array with one or more electrode extending therefrom, the array being in electrical communication with the circuit board, and a battery pack. The battery pack including a battery housing at least partially positioned within the housing, a plurality of battery cells positioned within the battery pack housing, a first power lead in electrical communication with the circuit board, a second power lead coupled to and extending between the plurality of battery cells and the circuit board, a safety switch positioned within the battery housing, the safety switch operably coupled between the first power lead and the plurality of battery cells, where the safety switch is adjustable between an ON state, where the plurality of battery cells are in electrical communication with the first power lead, and an OFF state where the plurality of battery cells are not in electrical communication with the first power lead, a controller positioned within the battery housing and in operable communication with the safety switch, the controller configured to detect one or more operating conditions, and where the controller is configured to adjust the safety switch between the ON state and the OFF state based at least in part on the detected operating conditions, and a power switch positioned within the battery housing, and where at least one of the operating conditions includes the state of the power switch.

DETAILED DESCRIPTION

Figure 1:
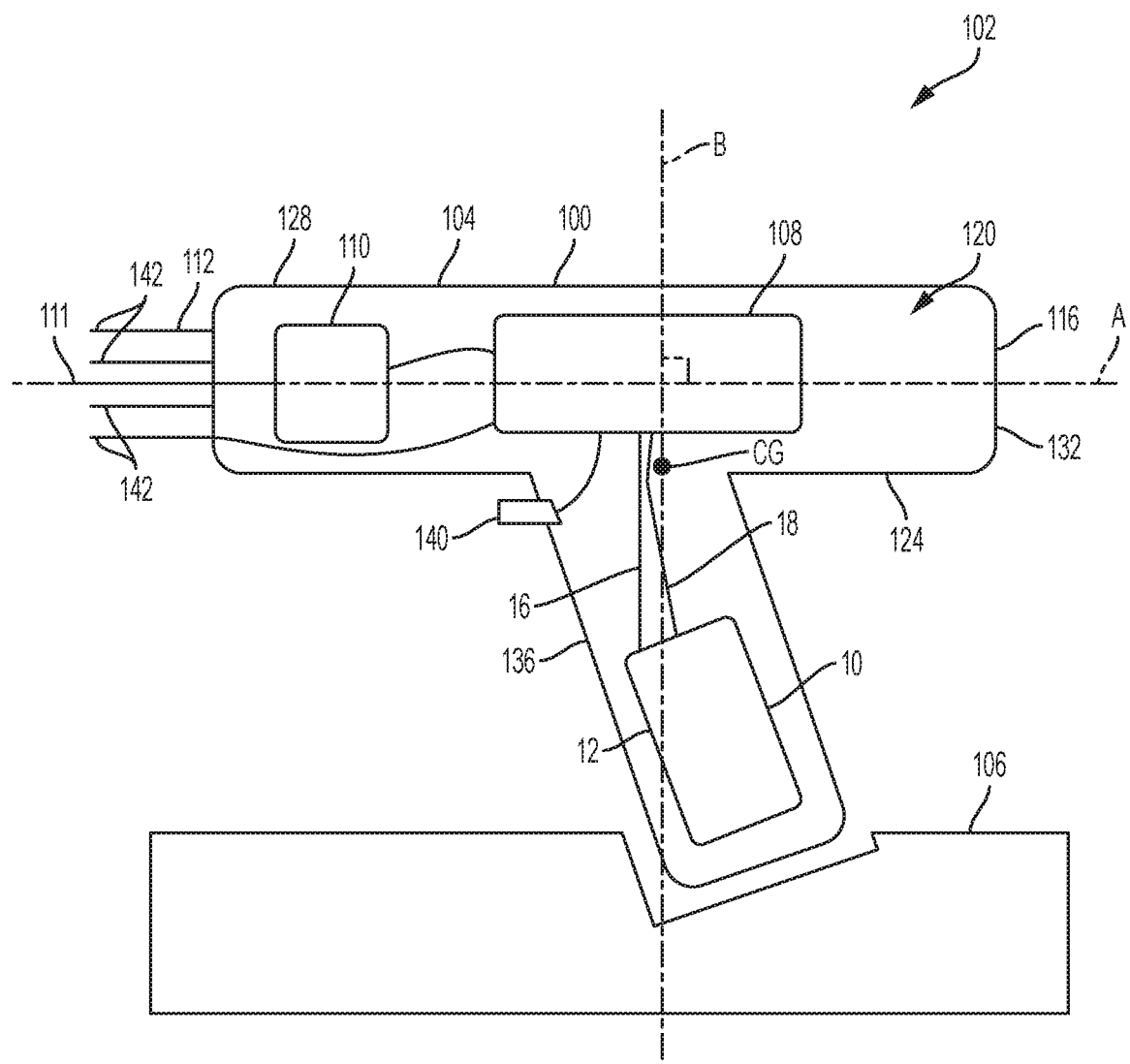
FIG. 1 is a schematic view of an electroporation unit showing a handset and a base unit in a docked configuration.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

It should also be noted that a plurality of other structural components may be utilized to implement the invention.

Furthermore, and as described in subsequent paragraphs, the specific configurations illustrated in the drawings are intended to exemplify embodiments of the invention. Alternative configurations are possible.

"Agent" may mean a polypeptide, a polynucleotide, a small molecule, or any combination thereof. The agent may be a recombinant nucleic acid sequence encoding an antibody, a fragment thereof, a variant thereof, or a combination thereof, as detailed in PCT/US2014/070188, which is incorporated herein by reference. "Agent" may mean a composition comprising a polypeptide, a polynucleotide, a small molecule, or any combination thereof. The composition may comprise a recombinant nucleic acid sequence encoding an antibody, a fragment thereof, a variant thereof, or a combination thereof, as detailed in PCT/US2014/070188, which is incorporated herein by reference. The agent may be formulated in water or a buffer, for example. The buffer may be saline-sodium citrate (SSC) or phosphate-buffered saline (PBS), for example. The ionic content of the buffers may increase conductivity, resulting in increased current flow in the targeted tissue. The concentration of the formulated polynucleotide may be between 1 μg and 20 mg/ml. The concentration of the formulated polynucleotide may be 1 μg/ml, 10 μg/ml, 25 μg/ml, 50 μg/ml, 100 μg/ml, 250 μg/ml, 500 μg/ml, 750 μg/ml, 1 mg/ml, 10 mg/ml, 15 mg/ml, or 20 mg/ml, for example.

A "peptide," "protein," or "polypeptide" as used herein can mean a linked sequence of amino acids and can be natural, synthetic, or a modification or combination of natural and synthetic.

"Polynucleotide" or "oligonucleotide" or "nucleic acid" as used herein means at least two nucleotides covalently linked together. A polynucleotide can be single stranded or double stranded, or can contain portions of both double stranded and single stranded sequence. The polynucleotide can be DNA, both genomic and cDNA, RNA, or a hybrid. The polynucleotide can contain combinations of deoxyribo- and ribo-nucleotides, and combinations of bases including uracil, adenine, thymine, cytosine, guanine, inosine, xanthine hypoxanthine, isocytosine, isoguanine, and synthetic or non-naturally occurring nucleotides and nucleosides. The polynucleotide may be a vector. Polynucleotides can be obtained by chemical synthesis methods or by recombinant methods.

"Vector" as used herein means a nucleic acid sequence containing an origin of replication. A vector can be a viral vector, bacteriophage, bacterial artificial chromosome, or yeast artificial chromosome. A vector can be a DNA or RNA vector. A vector can be a self-replicating extrachromosomal vector, and preferably, is a DNA plasmid.

The term "electroporation," ("EP") as used herein refers to the use of an electric field pulse to induce reversible microscopic pathways (pores) in a bio-membrane; their presence allows agents to pass from one side of the cellular membrane to the other.

During the electroporation process, electrodes in contact with target tissue and other elements of the electroporation device require electrical power to produce the necessary electroporation effect. In instances of a handheld electroporation device, the power necessary to drive these elements is provided by one or more battery packs that, in turn, are in electrical communication with one or more relatively fragile circuit boards. During the manufacturing process of the electroporation device, charged battery packs must be soldered to the circuit boards to make a connection that is sufficiently free of electrical inefficiencies to permit the battery pack to satisfy the relatively large electrical loads necessary to create the electroporation signal. Furthermore, the connection between the battery pack and the circuit board must be sufficiently small to allow the battery pack to be positioned within the device and maintain the proper center of gravity and ergonomics during use.

In some conventional systems, electrical components (i.e., resistors) are coupled to a circuit board to prevent battery packs from causing short circuits when they are installed. Such electrical components provide adequate resistance to prevent short circuits from occurring on the circuit boards when the battery packs are soldered but also create inefficiencies that would hamper the battery pack's ability to provide sufficient power to allow the device to produce the necessary electroporation signal. In other conventional systems, external switches are coupled to the circuit boards. The external switches are separate from the battery packs and connected in series with one of the leads from the battery packs. The external switches prevent the battery packs from electrically connecting to the circuit boards until the external switches are closed. However, external switches sufficiently strong to carry the electrical loads required for electroporation are generally too large and inefficient for use. For example, even while in a closed position, an external switch causes a voltage drop that reduces the voltage provided to the circuit board. Further still, accommodating such switches negatively affect both the ergonomics and the center of gravity of the electroporation device.

The present invention relates to a handset 100 of an electroporation device 102 with a battery pack 10. Illustrated in FIG. 1, the electroporation device 102 includes a base unit 106, and a handset 100 that may be detachably docked to the base unit 106. The base unit 106 is generally positioned on a table or other flat surface and is in electrical communication with and able to charge the battery pack 10 of the handset 100 when the two are in a docked or coupled configuration.

Illustrated in FIG. 1, the handset 100 of the electroporation device 102 includes a housing 104, a circuit board 108 at least partially positioned within the housing 104, an electrode array 112 in electrical communication with the circuit board 108, and a battery pack 10 in electrical communication with the circuit board 108. The handset 100 also includes an injection assembly 110 to administer agent to the target tissue via a hypodermic needle 111. The handset 100 facilitates the introduction of biomolecules into the cells of a target tissue (for example, skin) of a mammal using electroporation pulses generated by the circuit board 108 and relayed to the target tissue via the electrode array 112. During administration of the electroporation treatment, the battery pack 10 stores and supplies electrical power to the handset 100.

As shown in FIG. 1, the housing 104 of the handset 100 is formed from two halves or members 116 coupled together to form a volume 120 therebetween. Specifically, the members 116 form a pistol-shape having an upper portion 124 with a front end 128 and a rear end 132, and a handle portion 136 extending from the upper portion 124 to form a distal end. The handle portion 136 is sized and shaped to permit maximum ergonomic comfort for the user when grasping the handset 100. The handle portion 136 is also sufficiently small in cross-sectional shape to assure the user can grasp the handle portion 136 while also actuating the trigger 140 positioned proximate the intersection of the handle portion 136 and the upper portion 124 near the front end 128 to allow single-handed operation of the handset 100. While the housing 104 of the handset 100 is illustrated in the pistol-shape, it is to be understood that the housing 104 may include additional shapes or accommodate different grip styles.

In the illustrated embodiment, the housing members 116 include a plurality of mounting points (not shown) for positioning and securing the battery pack 10 within the handle portion 136 of the housing 104. More specifically, the mounting points position the battery pack 10 such that the overall center of gravity (CG) of the handset 100 is proximate the intersection between the upper portion 124 and the handle portion 136. In other embodiments, the upper portion 124 of the housing 104 may define an axis A extending longitudinally therethrough such that an axis B positioned perpendicular to axis A and passing through the center of gravity (CG) also passes through the handle portion 136 of the housing 104 (see FIG. 1).

The circuit board 108 of the handset 100 is at least partially positioned within the volume 120 of the housing 104 and in electrical communication with the battery pack 10, the electrode array 112, and the trigger 140. During use, the circuit board 108 receives electrical power from the battery pack 10 and selectively outputs an electroporation signal to the electrode array 112 based at least in part on inputs from the trigger 140.

The electrode array 112 includes a plurality of electrodes 142 each extending outwardly from the front end 128 of the upper portion 124 of the housing 104. Each electrode 142 is in electrical communication with the circuit board 108 and configured to convey the electroporation signal to the target tissue.

Figure 2:
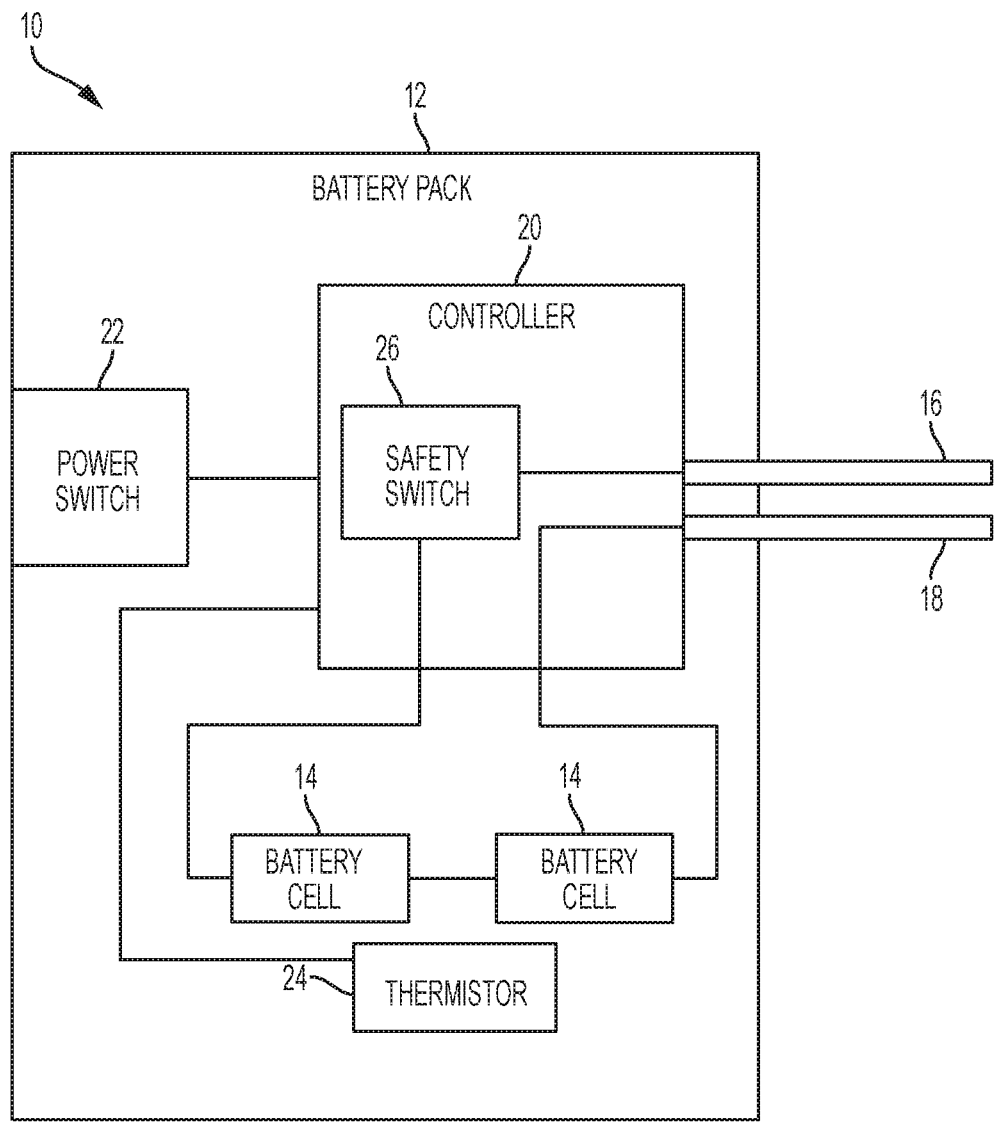
FIG. 2 is a block diagram of the battery pack of FIG. 1.

FIG. 2 illustrates the battery pack 10 of the handset 100. The battery pack 10 includes, among other things, a battery housing 12, a plurality of battery cells 14, a first power lead 16, a second power lead 18, a controller 20 including a safety switch 26, a power switch 22 in electrical communication with the controller 20, and a thermistor 24. In the illustrated construction, the plurality of battery cells 14, the controller 20, the safety switch 26, the power switch 22, and the thermistor 24 are all disposed within the battery housing 12. During use, the addition of the power switch 22 permits the user to manually disable the power flow between the battery cells 14 and the first power lead 16 without the need for additional, external switches or connectors. As such, the battery pack 10 may be installed in the housing 104 of the handset 100 without damaging the control circuits or circuit boards while also minimizing any power losses associated with circuitry positioned outside the housing 12.

As illustrated in FIG. 2, the plurality of battery cells 14 of the battery pack 10 includes two battery cells wired in series. However, in alternative embodiments more or fewer cells may be present dependent upon the specific power needs of the device in which the battery pack 10 is installed. In some embodiments, the plurality of battery cells 14 include a type of rechargeable battery such as, for example, lithium-ion, lead-acid, nickel cadmium, nickel metal hydride, etc. Lithium-ion batteries are smaller and lighter than conventional lead-acid batteries.

The first and second power leads 16 and 18 of the battery pack 10 electrically connect the battery cells 14 and controller 20 with the circuit board 108 of the handset 100. In the illustrated construction, the leads 16, 18 are soldered to the circuit board 108. By soldering the leads 16, 18 directly to the circuit board 108, space is saved over other types of electrical couplings, such as releasable connectors and the like. Furthermore, soldering minimizing any electrical losses that may occur if a connector or other external component is positioned between the battery pack 10 and the circuit board 108.

The thermistor 24 of the battery pack 10 is also positioned within the battery housing 12. During use, the thermistor 24 is configured to monitor the temperature of the battery pack 10. As shown in FIG. 2 the thermistor includes an external lead in electrical communication with the controller 20.

Illustrated in FIG. 2, the safety switch 26 selectively connects and disconnects the plurality of battery cells 14 from the first power lead 16 based at least in part on inputs from the controller 20. The safety switch 26 is adjustable between a connected configuration, where the plurality of battery cells 14 are in electrical communication with the power lead 16, and a disconnected configuration, where the plurality of battery cells 14 are not in electrical communication with the power lead 16. The safety switch 26 may include permanent fuses, resettable fuses, and/or switches. The wire trace lengths between the safety switch 26 and the plurality of battery cells 14 are shorter than those of external hardware or switches. Short wire trace lengths reduce the effects of voltage losses (i.e., IR voltage losses) and noise (i.e., switching noise) on the operation and efficiency of the battery pack 10. In addition, the safety switch 26 has a small footprint, being positioned completely within the battery housing 12 of the battery pack 10.

Illustrated in FIG. 2, the controller 20 of the battery pack 10 is configured to determine a plurality of operating conditions of the battery pack 10 and operate the safety switch 26 based at least in part on the information collected. The controller 20 may include an electronic processor (for example, a microprocessor, a microcontroller, or another suitable programmable device) and a memory. In some embodiments, the plurality of operating conditions may include, among other things, an over temperature condition, an over current condition, an over voltage condition, an under voltage condition, and the like.

During use, the controller 20 is configured to operate the safety switch 26 based at least in part on the detection of the plurality of operation conditions to prevent damage resulting from undesired operating conditions of the battery pack 10. For example, the controller 20 may operate the safety switch 26 to disconnect the plurality of battery cells 14 from the first power lead 16 when an over current condition is detected. In some embodiments, the controller 20 is configured to detect the plurality of operating conditions using a plurality of sensors (not shown) included in the controller 20. The plurality of sensors may include, among other things, voltage sensors, current sensors, temperature sensors, and the like.

Figure 3:
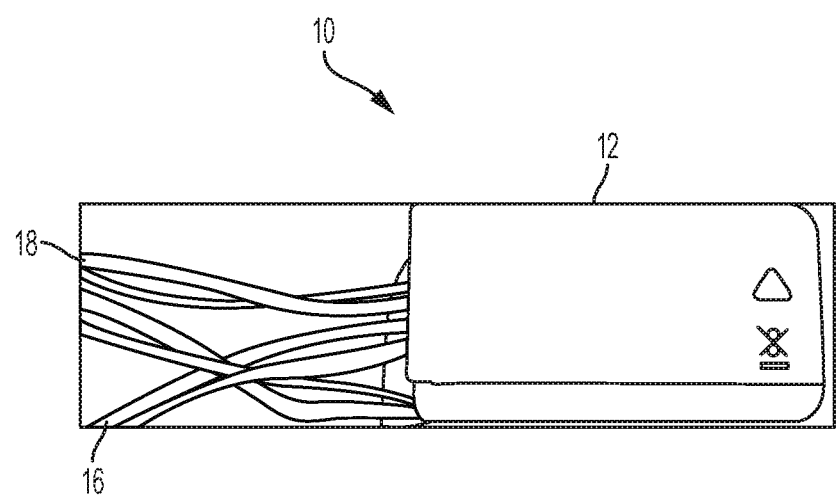
FIG. 3 is an image of the battery pack of FIG. 1, in accordance with some embodiments.
Figure 4:
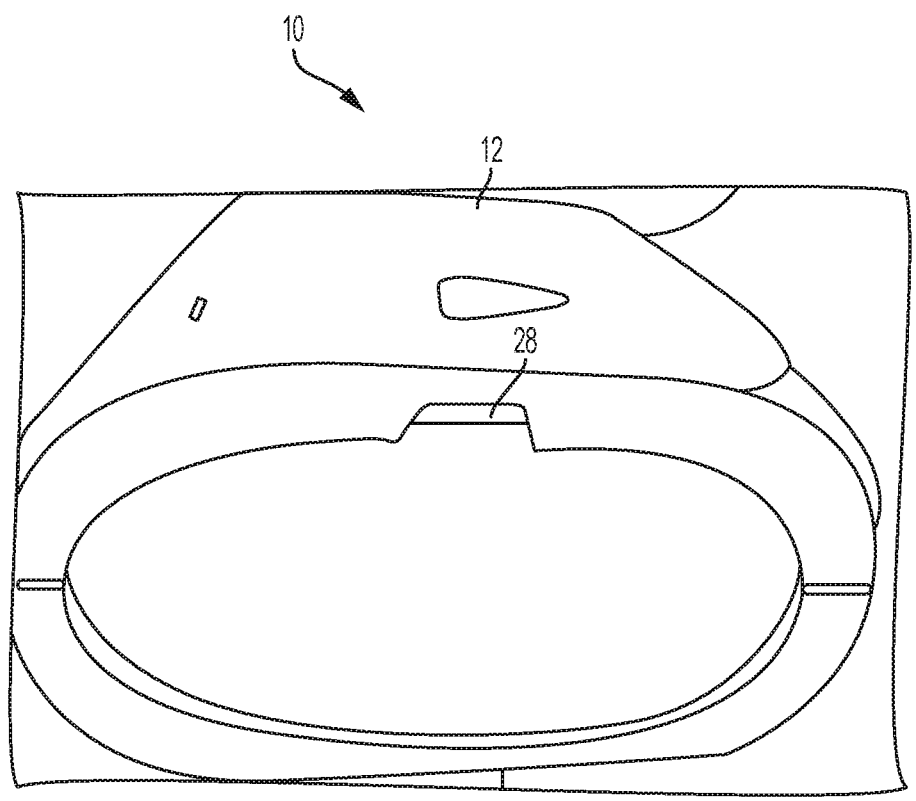
FIG. 4 is an image of the battery pack of FIG. 1, in accordance with some embodiments.

Illustrated in FIGS. 2-4, the power switch 22 of the battery pack 10 is in operable communication with the controller 20 and is manually adjustable between an ON state and an OFF state. During use, the controller 20 monitors the position of the power switch 22 similar to the other operating conditions described above. For example, detection that the power switch 22 is in the OFF state causes the controller 20 to trigger the safety switch 26 and disconnect the plurality of battery cells 14 from the first power lead 16—in the same manner as if an undesired operating condition was detected. In such embodiments, the controller 20 further operates the safety switch 26 to connect the plurality of battery cells 14 to the first power lead 16 when the power switch 22 is in the ON state. In alternate embodiments, the controller 20 operates the safety switch 26 to disconnect the plurality of battery cells 14 from the first power lead 16 when the power switch 22 is in the ON state. In such alternate embodiments, the controller 20 further operates the safety switch 26 to connect the plurality of battery cells 14 to the first power lead 16 when the power switch 22 is in the OFF state.

Illustrated in FIG. 4, the power switch 22 is disposed within the housing 12 of the battery pack 10 such that the switch 22 is externally accessible. In the illustrated embodiment, the power switch 22 is accessible through a hole 28 formed in the housing 12. A user can change the state of the power switch 22 by manipulating the position of the power switch 22 using, for example, a small screwdriver or tweezers. In other embodiments, the power switch 22 may be an electromechanical switch or a magnetic switch. In such embodiments, a magnet may be used to switch the power switch 22 between the ON state and the OFF state. Because the power switch 22 is externally accessible, it can be switched to the OFF state during the manufacturing process to allow the battery pack 10 to be installed on a circuit board without causing a short circuit as explained above. Once installation is complete, the power switch 22 can be switched to the ON state to allow the battery pack 10 to supply electrical power to the circuit board.

Accordingly, in devices that include several circuit boards, the power switch 22 permits installation of the battery pack 10 prior to having a final circuit board configuration assembled. By allowing the battery pack 10 to be installed earlier in the installation process, more working space is provided making the installation process easier and more efficient. In contrast, in instances where the battery pack 10 must be installed as a final step after the final circuit board configuration is assembled, it may be difficult to install the battery pack 10 due to the limited space available.

As described above, the power switch 22 is not connected in series with the plurality of battery cells 14, but rather communicates with the controller 20 so as to manipulate the safety switch 26 indirectly. As such, the power switch 22 acts as an additional operating condition in addition to those typically found in a battery pack. Therefore, the power switch 22 of the present invention provides the user with a manual way to disengage the plurality of battery cells 14 from the leads 16, 18 without adversely affecting the performance of the battery pack 10 and maintaining a small overall foot print for the battery pack 10.

Thus, the invention provides, among other things, a power switch 22 for controlling a battery pack 10. Various features and advantages of the invention are set forth in the following claims.

The foregoing description of the specific aspects will so fully reveal the general nature of the invention that others can, by applying knowledge within the skill of the art, readily modify and/or adapt for various applications such specific aspects, without undue experimentation, without departing from the general concept of the present disclosure. Therefore, such adaptations and modifications are intended to be within the meaning and range of equivalents of the disclosed aspects, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary aspects, but should be defined only in accordance with the following claims and their equivalents.

All publications, patents, patent applications, and/or other documents cited in this application are incorporated by reference in their entirety for all purposes to the same extent as if each individual publication, patent, patent application, and/or other document were individually indicated to be incorporated by reference for all purposes.

For reasons of completeness, various aspects of the invention are set out in the following numbered clauses:

Clause 1. A handset of an electroporation device, the handset comprising:
a housing defining a volume therein;
a circuit board at least partially positioned within the volume;
an electrode extending from the housing and in electrical communication with the circuit board; and
a battery pack including:
a battery pack housing,
a plurality of battery cells positioned within the battery pack housing,
a first power lead in electrical communication with the circuit board,
a second power lead coupled to the plurality of battery cells and in electrical communication with the circuit board, a safety switch positioned within the battery pack housing and coupled between the first power lead and the plurality of battery cells, wherein the safety switch is adjustable between an ON state, where the plurality of battery cells are in electrical communication with the first power lead, and an OFF state, where the plurality of battery cells are not in electrical communication with the first power lead.

Clause 2. The handset of clause 1, wherein the battery pack is at least partially positioned within the volume.

Clause 3. The handset of clause 1, wherein the housing includes an upper portion and a handle portion extending from the upper portion, and wherein the battery pack is at least partially positioned within the handle portion of the housing.

Clause 4. The handset of clause 1, wherein the housing includes an upper portion and a handle portion extending from the upper portion, and wherein the center of gravity of the electroporation device is positioned proximate the intersection of the upper portion and the handle portion.

Clause 5. The handset of clause 1, wherein the battery pack further includes a controller configured to detect a plurality of operating conditions, and wherein the controller adjusts the safety switch between the ON state and the OFF state based at least in part on the operating conditions.

Clause 6. The handset of clause 5, wherein the operating conditions include at least one of an over temperature condition, an over current condition, an over voltage condition, and an under voltage condition.

Clause 7. The handset of clause 5, wherein the battery pack further includes a power switch adjustable between an ON state and an OFF state, and wherein at least one of the operating conditions includes the state of the power switch.

Clause 8. The handset of clause 7, wherein the power switch is located inside the battery housing.

Clause 9. The handset of clause 8, wherein the power switch is accessible from outside the battery housing.

Clause 10. The handset of clause 1, wherein the battery pack further includes a power switch accessible from outside the battery housing and adjustable between an ON state and an OFF state, and wherein the safety switch is adjustable between the ON state and the OFF state based at least in part on the state of the power switch.

Clause 11. The handset of clause 1, wherein the first lead is soldered to the circuit board, and wherein the second lead is soldered to the circuit board.

Clause 12. A handset of an electroporation device, the handset comprising:
 a housing;
 an injection assembly;
 a circuit board at least partially positioned within the housing and in operable communication with the injection assembly;
 an electrode extending from the housing and in electrical communication with the circuit board; and
  a battery pack including:
   a battery housing at least partially positioned within the housing,
   a plurality of battery cells positioned within the battery pack housing,
   a first power lead in electrical communication with the circuit board,
   a second power lead coupled to and extending between the plurality of battery cells and the circuit board,
   a safety switch operable coupled between the first power lead and the plurality of battery cells, wherein the safety switch is adjustable between an ON state, where the plurality of battery cells are in electrical communication with the first power lead, and an OFF state where the plurality of battery cells are not in electrical communication with the first power lead, and
   a controller in operable communication with the safety switch, the controller configured to detect one or more operating conditions, and wherein the controller is configured to adjust the safety switch between the ON state and the OFF state based at least in part on the detected operating conditions.

Clause 13. The handset of clause 12, wherein the safety switch is positioned within the battery housing.

Clause 14. The handset of clause 12, wherein the battery pack further includes a power switch positioned within the battery housing, and wherein at least one of the operating conditions is the state of the power switch.

Clause 15. The handset of clause 14, wherein the battery housing defines an aperture, and wherein the power switch is accessible from outside the battery housing via the aperture.

Clause 16. The handset of clause 12, wherein the operating conditions include at least one of an over temperature condition, an over current condition, an over voltage condition, and an under voltage condition.

Clause 17. The handset of clause 12, wherein the controller is positioned within the battery housing.

Clause 18. The handset of clause 12, wherein the housing includes an upper portion and a handle portion extending from the upper portion, and wherein the battery pack is positioned within the handle portion.

Clause 19. An electroporation device comprising:
 a base station;
 a handset removably coupled to the base station, the handset including:
  a housing,
  an injection assembly,
  a circuit board at least partially positioned within the housing and in operable communication with the injection assembly,
  an array with one or more electrode extending therefrom, the array being in electrical communication with the circuit board, and
  a battery pack including:
   a battery housing at least partially positioned within the housing,
   a plurality of battery cells positioned within the battery pack housing,
   a first power lead in electrical communication with the circuit board,
   a second power lead coupled to and extending between the plurality of battery cells and the circuit board,
   a safety switch positioned within the battery housing, the safety switch operably coupled between the first power lead and the plurality of battery cells, wherein the safety switch is adjustable between an ON state, where the plurality of battery cells are in electrical communication with the first power lead, and an OFF state where the plurality of battery cells are not in electrical communication with the first power lead,
   a controller positioned within the battery housing and in operable communication with the safety switch, the controller configured to detect one or more operating conditions, and wherein the controller is configured to adjust the safety switch between the ON state and the OFF state based at least in part on the detected operating conditions, and
   a power switch positioned within the battery housing, and wherein at least one of the operating conditions includes the state of the power switch.

Clause 20. The electroporation device of clause 19, wherein the battery housing is positioned within the housing such that the center of gravity of the electroporation device is vertically aligned with the battery pack.

Clause 21. The electroporation device of clause 19, wherein the base station is in electrical communication with the battery pack when the handset is coupled to the base station.

What is claimed is:

1. A handset of an electroporation device, the handset comprising:
 a housing defining a volume therein;
 a circuit board at least partially positioned within the volume;
 an electrode extending from the housing and in electrical communication with the circuit board; and
 a battery pack including:
  a battery pack housing,
  a plurality of battery cells positioned within the battery pack housing,
  a first power lead in electrical communication with the circuit board,
  a second power lead coupled to the plurality of battery cells and in electrical communication with the circuit board,
  a safety switch positioned within the battery pack housing and coupled between the first power lead and the plurality of battery cells, wherein the safety switch is adjustable between an ON state, where the plurality of battery cells are in electrical communication with the first power lead, and an OFF state, where the plurality of battery cells are not in electrical communication with the first power lead, and
  a power switch positioned within the battery pack housing, wherein the power switch is accessible from outside the battery pack housing and is adjustable between an ON state and an OFF state, and wherein the safety switch is adjustable between its ON state and its OFF state based at least in part on the state of the power switch.

2. The handset of claim 1, wherein the battery pack is at least partially positioned within the volume.

3. The handset of claim 1, wherein the housing includes an upper portion and a handle portion extending from the upper portion, and wherein the battery pack is at least partially positioned within the handle portion of the housing.

4. The handset of claim 1, wherein the housing includes an upper portion and a handle portion extending from the upper portion, and wherein the center of gravity of the handset is positioned proximate an intersection of the upper portion and the handle portion.

5. The handset of claim 1, wherein the battery pack further includes a controller configured to detect a plurality of operating conditions, and wherein the controller adjusts the safety switch between the ON state and the OFF state based at least in part on the operating conditions.

6. The handset of claim 5, wherein the operating conditions include at least one of an over temperature condition, an over current condition, an over voltage condition, and an under voltage condition.

7. The handset of claim 5, wherein at least one of the operating conditions includes the state of the power switch.

8. The handset of claim 1, wherein the first power lead is soldered to the circuit board, and wherein the second power lead is soldered to the circuit board.

9. A handset of an electroporation device, the handset comprising:
a housing;
an injection assembly;
a circuit board at least partially positioned within the housing and in operable communication with the injection assembly;
one or more electrodes extending from the housing and in electrical communication with the circuit board; and
a battery pack including:
a battery pack housing at least partially positioned within the housing,
a plurality of battery cells positioned within the battery pack housing,
a first power lead in electrical communication with the circuit board,
a second power lead coupled to and extending between the plurality of battery cells and the circuit board,
a safety switch coupled between the first power lead and the plurality of battery cells, wherein the safety switch is adjustable between an ON state, where the plurality of battery cells are in electrical communication with the first power lead, and an OFF state where the plurality of battery cells are not in electrical communication with the first power lead,
a power switch positioned within the battery pack housing, wherein the power switch is accessible from outside the battery pack housing and is adjustable between an ON state and an OFF state, and wherein the safety switch is adjustable between its ON state and its OFF state based at least in part on the state of the power switch, and
a controller in operable communication with the safety switch, the controller configured to detect one or more operating conditions, and wherein the controller is configured to adjust the safety switch between the ON state and the OFF state based at least in part on the detected operating conditions.

10. The handset of claim 9, wherein the safety switch is positioned within the battery pack housing.

11. The handset of claim 9, wherein at least one of the one or more operating conditions is the state of the power switch.

12. The handset of claim 11, wherein the battery pack housing defines an aperture, and wherein the power switch is accessible from outside the battery pack housing via the aperture.

13. The handset of claim 9, wherein the operating conditions include at least one of an over temperature condition, an over current condition, an over voltage condition, and an under voltage condition.

14. The handset of claim 9, wherein the controller is positioned within the battery pack housing.

15. The handset of claim 9, wherein the housing includes an upper portion and a handle portion extending from the upper portion, and wherein the battery pack is positioned within the handle portion.

16. An electroporation device comprising:
a base station; and
a handset removably coupled to the base station, the handset including:
a housing,
an injection assembly,
a circuit board at least partially positioned within the housing and in operable communication with the injection assembly,
an array with one or more electrodes extending therefrom, the array being in electrical communication with the circuit board, and
a battery pack including:
a battery pack housing at least partially positioned within the housing,
a plurality of battery cells positioned within the battery pack housing,
a first power lead in electrical communication with the circuit board,
a second power lead coupled to and extending between the plurality of battery cells and the circuit board,
a safety switch positioned within the battery pack housing, the safety switch operably coupled between the first power lead and the plurality of battery cells, wherein the safety switch is adjustable between an ON state, where the plurality of battery cells are in electrical communication with the first power lead, and an OFF state where the plurality of battery cells are not in electrical communication with the first power lead,
a controller positioned within the battery pack housing and in operable communication with the safety switch, the controller configured to detect one or more operating conditions, and wherein the controller is configured to adjust the safety switch between the ON state and the OFF state based at least in part on the detected operating conditions, and
a power switch positioned within the battery pack housing, wherein the power switch is accessible from outside the battery pack housing, and wherein at least one of the operating conditions includes the state of the power switch.

17. The electroporation device of claim 16, wherein the battery pack housing is positioned within the housing such that the center of gravity of the handset is vertically aligned with the battery pack.

18. The electroporation device of claim 16, wherein the base station is in electrical communication with the battery pack when the handset is coupled to the base station.

* * * * *